US006422253B1

(12) United States Patent
Glynn et al.

(10) Patent No.: US 6,422,253 B1
(45) Date of Patent: Jul. 23, 2002

(54) MECHANIZED FUMIGATION TENT WITH COMPOSITE CLOSING STRUCTURE

(75) Inventors: Kenneth P. Glynn, Raritan, NJ (US); Christopher D. Langhart, New Hope, PA (US)

(73) Assignee: Western Industries, Inc., Lester, PA (US)

( * ) Notice: Subject to any disclaimer, the term of this patent is extended or adjusted under 35 U.S.C. 154(b) by 0 days.

(21) Appl. No.: 09/909,321

(22) Filed: Oct. 2, 2001

Related U.S. Application Data

(63) Continuation-in-part of application No. 09/752,387, filed on Dec. 29, 2000.

(51) Int. Cl.[7] .............................................. E04H 15/54
(52) U.S. Cl. ...................... 135/115; 135/905; 422/294; 422/292; 422/28; 422/32; 426/320
(58) Field of Search ............................... 135/115, 905; 422/28, 32, 33, 292, 294, 306; 426/320, 331, 333, 335; 160/19

(56) References Cited

U.S. PATENT DOCUMENTS

| 645,890 A | * | 3/1900 | Conrad | 135/905 |
|---|---|---|---|---|
| 4,033,367 A | * | 7/1977 | Johnston | 135/115 |
| 4,229,914 A | * | 10/1980 | Lucas | 135/115 |
| 5,641,463 A | * | 6/1997 | Langhart | 422/294 |
| 5,918,614 A | * | 7/1999 | Lynch | 135/115 |
| 5,964,236 A | * | 10/1999 | Berke | 135/115 |
| 5,974,740 A | * | 11/1999 | Park | 135/115 |

FOREIGN PATENT DOCUMENTS

| JP | 692465 | * | 4/1994 | 135/115 |
|---|---|---|---|---|

* cited by examiner

*Primary Examiner*—Beth A. Stephan
(74) *Attorney, Agent, or Firm*—Kenneth P. Glynn, Esq.

(57) ABSTRACT

The present invention provides a mechanized fumigation tent with a composite closing structure. The composite closing structure is connected to the bottom perimeter of side curtains for sealing the bottom perimeter of the side curtains. The composite closing structure has at least a first component and second component. The first component is a structural support component and has sufficient rigidity to flex no greater than 6 inches over a 10 foot length with a fulcrum weight of 100 pounds. The second component is a sealing component and is formed of flexible material. Further, the sealing component may be a flexible base mounted along the bottom perimeter for receiving, holding and releasing water from an external water supply. When the sealing component holds water, it will seal the tent to a floor. In a preferred embodiment, the structural support component is formed of a triangular cross-sectional shape. The structural support component may be embedded within the sealing component or connected to an outside of the sealing component.

20 Claims, 7 Drawing Sheets

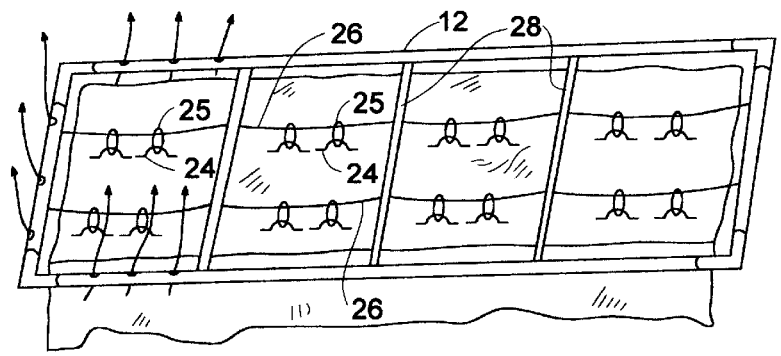
FIG. 3 PRIOR ART
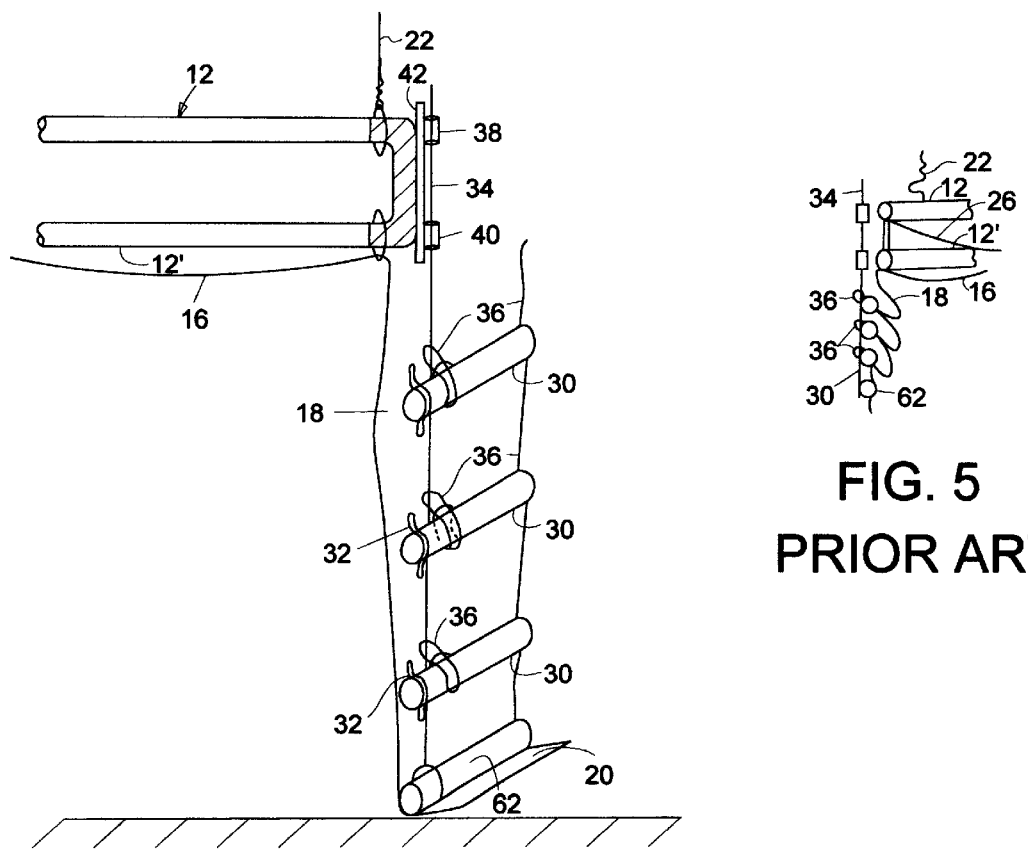
FIG. 5 PRIOR ART
FIG. 4 PRIOR ART

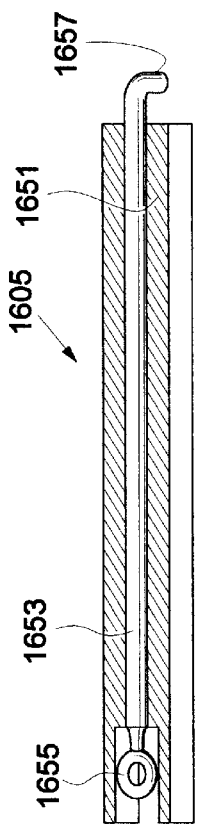
FIG. 8
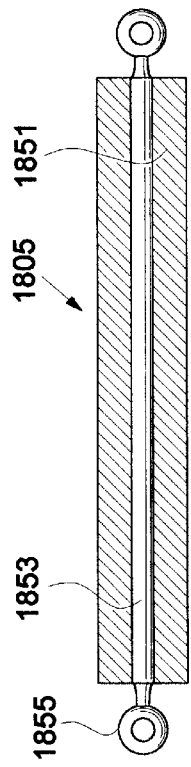
FIG. 9
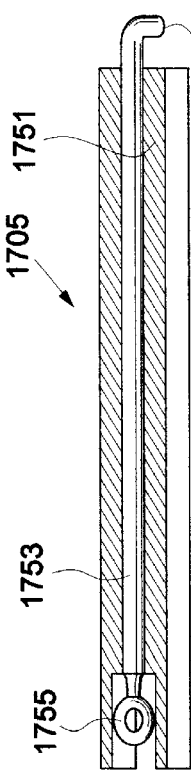
FIG. 10
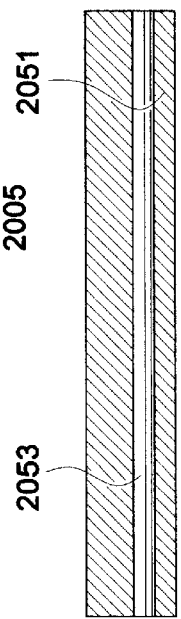
FIG. 11
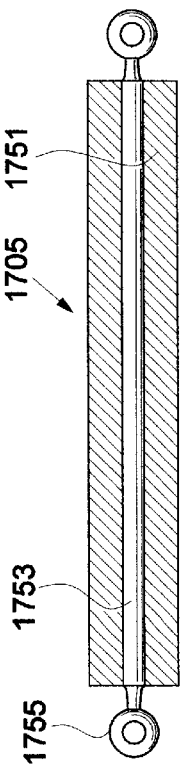
FIG. 12
FIG. 13

FIG. 15
FIG. 16
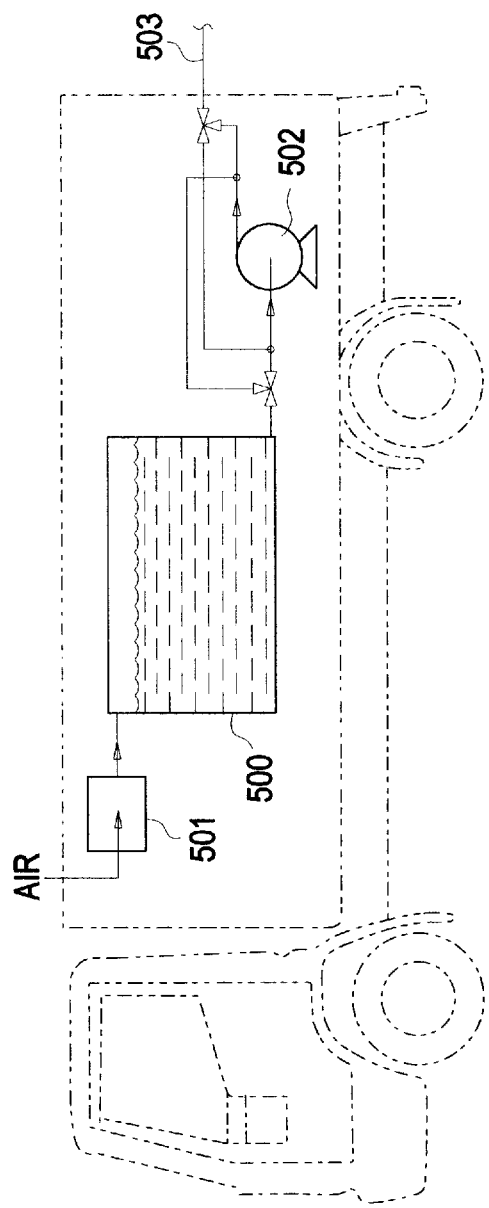
FIG. 17

MECHANIZED FUMIGATION TENT WITH COMPOSITE CLOSING STRUCTURE

REFERENCES TO RELATED APPLICATIONS

This application is a continuation-in-part of copending U.S. patent application Ser. No. 09/752,387, filed on Dec. 29, 2000, and entitled "Mechanized Fumigation Tent", by Christopher Langhart, one of the same inventor herein.

BACKGROUND OF THE INVENTION

1. Field of the Invention

The present invention relates to a mechanized tent. In particular, it relates to a mechanized tent having a frame and a collectable tarp attached to the frame which can be raised and lowered over pallets of produce or the like, particularly useful for fumigation of produce, e.g. imported products.

2. Information Disclosure Statement

Once fumigated, produce has a shelf life of at most ten days to two weeks. It is therefore desirable to fumigate the produce close to the place where it will be ultimately sold. For imported produce, this place is typically inside a dock building or warehouse located at a port of entry. Pallets of the produce are unloaded from a ship and placed or staged on the floor of the dock building.

Known methods of fumigating produce involve covering the pallets of produce with a polyethylene or plastic impregnated tarpaulin and then introducing a gas, e.g., methyl bromide, under the tarp to kill live insect infestations. Workers climb on top of the pallets or use poles to pull the tarp over a group of pallets. Because it is necessary for the gas to circulate freely on all sides and the top of the pallets, the tarp cannot lay flat on the top of the pallets. The United States Department of Agriculture requires that a space of about two feet be provided on the top of the pallets, and at least two feet on their sides to allow room for the placement of fans to facilitate the circulation of the fumigation gas. The fans may be tied down with rope to prevent them from moving. Several hoses for introducing the gas is secured to the top of selected fans. The volume of space under the tarp, i.e., the total cubic feet, determines how many fans and points of introduction are required.

One method for maintaining the required space on the top of the pallets is to erect wood frames in the shape of a "T" or an "A" at each corner and attach rope between each "T" or an "A" to create a web of support for the tarp. The side space is maintained by draping the tarp outward as it contacts the floor of the dock building and securing it in that position by placing flexible vinyl tubes (approximately 6" in diameter and 4' long) filled with sand on top of the edge of the tarp. At least 2 feet of excess tarp remains beyond the 'sand tubes'.

The steps involved in pulling the tarp over the pallets, setting up the fans, attaching the introduction hoses to the fans, handling hundreds of tubes of sand, and dismantling and storing all of the above equipment, and repeating the process upon completion, require many labor intensive hours.

Improvements to the conventional method of fumigating produce include permanently suspending the tarpaulin from an overhead frame and lowering the frame over the pallets as needed. Such a frame may be made from welded trusses to form a disassemble one piece unit of varying dimensions. The typical frame size may be 50 feet long by 250 feet wide, but may be larger or smaller depending upon the spacing between support columns in the dock building. To the underside of the frame a tarpaulin is attached which has been manufactured with grommets, i.e., tabs and eyelets, specific to the frame it hangs from.

The frame may be raised and lowered by a system of cables and pulleys located above the unit which are attached to exposed barjoists on the underside of the roof of the dock building. The cables are connected to hand-operated or motor-operated winces mounted on the support columns in the dock building. Workers simultaneously crank the winches to lower or raise the frame to a height above the pallets that allows the required 2 feet of space between the tarp and pallets of produce.

A typical tent may be lifted by twelve or more active pickup points. Between each of these points two counter-weight sandbags are deployed to offset the self-weight of the frame and the polyethylene enclosure. Each truss section of the frame spans approximately fifty feet with two mid-point sandbags. These tend to become hung up from friction and pull at an angle to prevent the sandbag from lowering onto the polyethylene enclosure as it is elevated.

A difficult and time-consuming job associated with operating such a system is gathering up the tarp which overhangs from the sides of the frame before the frame is raised. This is necessary because the typical dock building height of about twenty-two feet is limited to about eighteen feet by overhead piping, electrical conduits, etc. When the support frame is raised to the maximum height permitted by these obstructions the tarp hangs down low enough to catch the tops of forklift trucks as they move the pallets of produce in and out of the tent area.

One known way of gathering up the tarp on the sides is to run horizontal plastic pipes through double-thickness portions of the tent walls which form pockets. These pockets can be located at approximately one-third and two-thirds of the wall height and are tied up to the top framing with rope every ten feet or so. Pulled ropes raise the pockets and thus gather the sides of the tent. This method is also time-consuming, however, because it requires numerous tie-up procedures in order to completely raise the tent, e.g., usually at ten to twenty foot intervals around the tent perimeter.

U.S. Pat. No. 5,641,463 utilizes many of the aforementioned improved technique features and additionally incorporates unique features which are more fully discussed in conjunction with some of the drawings described below.

Notwithstanding the above prior art, there is no teaching which anticipates or renders the present invention obvious. Thus, it is neither taught nor suggested to use a system with a ceiling-mounted suspended frame with a fumigation tarp position atop the support frame in a sealed fashion having a composite closing structure.

SUMMARY OF THE INVENTION

It is an object of the present invention to provide a large mechanized fumigation tent which incorporates the height of the supporting frame within the tarp structure to eliminate the extra space otherwise needed when the support structure is stacked above the gathered, stored tarp.

It is another object of the present invention to decrease the total weight needed for an efficiently operated fumigation tent.

It is also an object of the present invention to provide a fumigation tent which does not require permanent water storage tanks, related plumbing or the otherwise necessary space which would be occupied by permanent water storage facilities.

It is yet another object of the present invention to provide a large fumigation tent for fumigating produce, logs, textiles, wood products, and other forms of potentially infested imports which can be quickly, conveniently and freely raised and lowered over pallets of the produce.

It is also an object of the present invention to provide a fumigation tent that does not interfere with the operation of forklift trucks as they move pallets of the produce in and out of a tent area and that does not require extensive tie-up procedures to accomplish this.

Another object of the present invention is to provide a fumigation tent which can be raised from a single remote location so that personnel need not be near the tent area after fumigation is complete since exposure to residual gas, which may not have been evacuated from some pallet areas, is possible and can be harmful.

It is yet another object of the present invention to provide for alternative mechanisms for first lifting side curtains of the tarp and then lifting the entire structure and, conversely, lowering the entire structure and then the side curtains of the tarp.

A further object of the present invention to provide a system which seals the tent to the floor of the dock building and which can be easily raised with tent.

The present invention provides a fumigation tent which includes a structure, support cables communicating with the structure, and a frame suspended from the structure by the support cables. The frame has an underside upon which a tarp is adapted to be mounted to the underside of the frame. The tarp hangs from the frame defining a tent having a top and side curtains. The side curtains have a lower periphery that defines a bottom perimeter. There is also a plurality of horizontal pipes attached to, and arranged along, the side curtains of the tent at spaced intervals between the bottom perimeter and the top of the tent. Moreover, there are a plurality of winch cables for raising the horizontal pipes, and rings, disposed around the winch cables and attached to the horizontal pipes, for gathering up and supporting the tarp as the horizontal pipes are raised. The rings and horizontal pipes cooperate with each other to collect the tarp into a plurality of small overhanging portions. A plurality of collapsible flexible hoses supply water from elevated storage tanks located above the tent to a composite closing structure.

The present invention also provides a composite closing structure connected to the bottom perimeter of side curtains or physically compressing against the floor, for sealing the bottom perimeter of the side curtains. The composite closing structure has at least a first component and second component. The first component is a structural support component and has sufficient rigidity to flex no greater than 6 inches over a 10 foot length with a fulcrum weight of 100 pounds. The second component is a sealing component and is formed of flexible material.

The sealing component may be flexible hosing, flexible synthetic foam, flexible rubber, or rubber foam. Further, the sealing component may be a flexible base mounted along the bottom perimeter for receiving, holding and releasing water from an external water supply. When the sealing component holds water, it will seal the tent to a floor.

In a preferred embodiment, the structural support component is formed of a triangular cross-sectional shape. In addition, the structural support component may be elongated metal sections, elongated wood sections, elongated plastic sections, and the like. Moreover, the structural support component may have various geometric shapes, including, but not limited to circular rectangular, hexagonal, octagonal, square, and the like. Furthermore, the structural support component may be within the sealing component or outside the sealing component.

The present invention further provides for attachment of the winch cables to clew plates which in turn are attached to winches by winch chains. Preferably, the winches are motorized and be operated by remote control. (This provides an important safety advantage, because personnel do not have to be near the tent while it is being raised. Therefore, personnel can avoid being exposed to any lingering fumigation gas which is hazardous.) It is also preferable that hand winches with cables be located near the motorized winches, so that they can be attached to the clew plates to provide emergency back up in case electrical problems occur.

Other advantages and characteristics of the present invention will become apparent in view of the description and accompanying drawings that follow.

BRIEF DESCRIPTION OF THE DRAWINGS

FIG. 3 is a top planar perspective view of the frame and the cables used to support the top middle portion of the prior art tent shown above;

FIG. 4 is a partial perspective view of a side curtain of the prior art tent shown above, with the horizontal bars and rings which are used to support and collect the side curtain while it is being raised;

FIG. 5 is a side perspective view of a portion of the above described prior art tent from U.S. Pat. No. 5,641,463 in its raised position;

FIG. 8 shows a front view in partial cross-section of the composite closing structure shown in FIG. 7;

FIG. 9 and FIG. 10 show front cross-sectional views of two composite closing structures of the present invention, each having a hook and eyelet for removably connecting each composite closing structure;

FIG. 11 and FIG. 12 show front cross-sectional views of another embodiment of two composite closing structures of the present invention, each having links for removably connecting each composite closing structure;

FIG. 13 shows a front cross sectional view of another embodiment of a composite closing structure of the present invention having a single structural support component within a single sealing component.

FIG. 15 and FIG. 16 show side views of a present invention composite closing structure which may be used in combination with the fumigation tent shown in FIG. 14; and FIG. 17 shows a water delivery system for filling bottom periphery flexible hosing with water for sealing curtain bottom areas.

DETAILED DESCRIPTION OF THE PRESENT INVENTION

Figure 1:
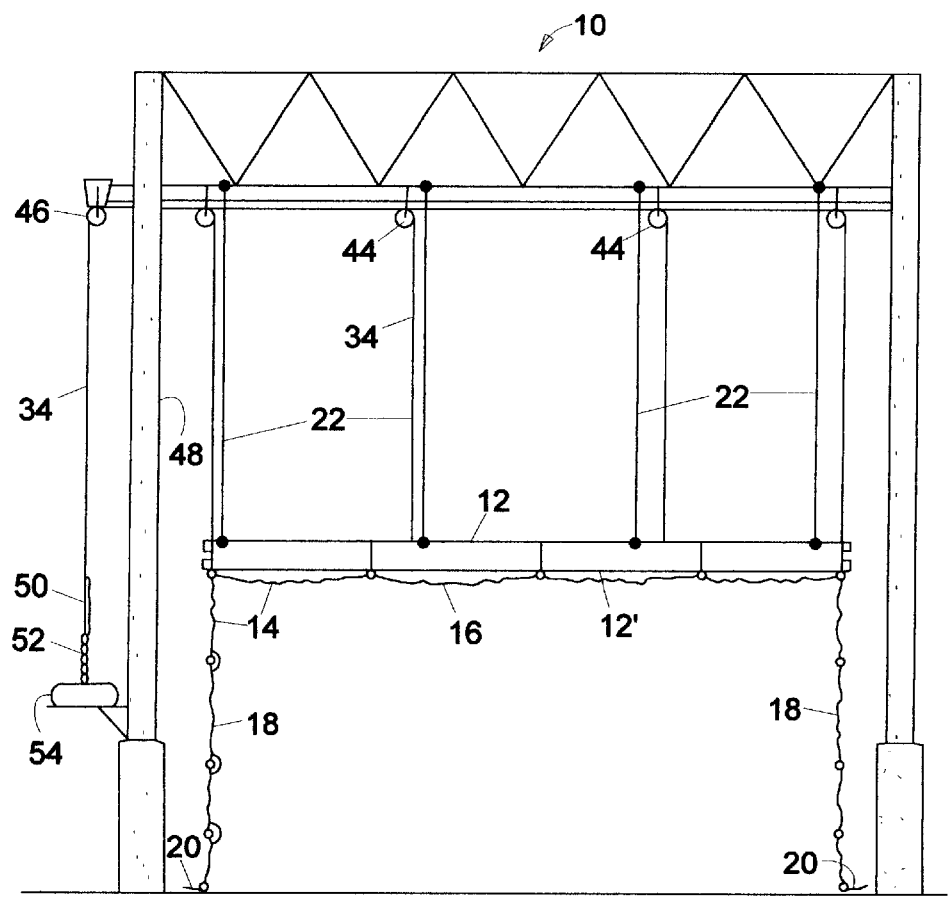
FIG. 1 is a cross-sectional schematic view of a fumigation tent in its lowered position from prior art U.S. Pat. No. 5,641,463.

Referring to the prior art drawings from U.S. Pat. No. 5,641,463 to the present invention herein, shown in the present as FIGS. 1 through 5, the following description is a summary thereof: In FIG. 1, a prior art apparatus for fumigating pallets of produce is indicated generally as apparatus 10. It has a support system for uniformly raising and lowering a tarp enclosure with motorized crank winches while maintaining required clearances, as well as for relocation of frame support cables to vertical positions above the lifting position.

Figure 2:
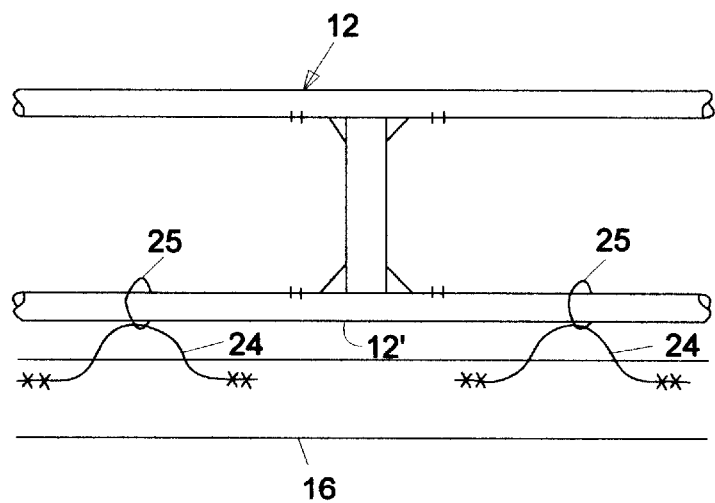
FIG. 2 is a partial side-sectional view of the frame of the tent in FIG. 1 as it is attached to the top portion of the prior art tent.

The apparatus 10 includes a frame 12 and a tarp 14 mounted to the frame underside with tabs 24 and eye rings 25. FIG. 2 shows detail of the top 16 being mounted. The tarp 14 forms a tent with flat top 16, and side curtains 18 having a lower periphery bottom perimeter 20. The frame 12 can be constructed out of aluminum pipes welded and bolted together in a truss-like configuration. However, as will be recognized by those skilled in the art, the frame can be of any shape and construction which is capable of carrying the weight of the tent. The frame 12 may be, for example, suspended from the roof of a dock building or warehouse by support cables 22.

The cables 26 hang between cross bars 28, spaced so that sagging of the top 16 is reduced, usually about every fifteen feet, along cross-sections of the frame 12, as shown in FIG. 3.

Horizontal pipes 30 are fitted into tarp pockets 32 formed in double-thickness portions of the side curtains 18, as shown in FIG. 4, located just above the bottom perimeter 20; approximately one-third of the distance between the first interval and the top 16; and approximately two-thirds of the distance between the first interval and the top 16. Winch cables 34 draw up the horizontal pipes 30. These cables pass through rings 36 attached along and at the ends of the horizontal pipes, as shown in FIG. 4. The tarp pockets 32 are gathered up by the pipes 30, and support the tarp 14 as the horizontal pipes are being raised. Each winch cable 34 passes through a pair of guide tubes 38 and 40 fixed to a plate 42 mounted on the frame 12, also shown in FIG. 4. Guide tubes 38 and 40 and plate 42 provide a means for enabling the frame to be lifted by the winch cables 34 once the horizontal pipes 30 are raised and the tarp is completely collected.

The winch cables 34 pass around roof-mounted pulleys 44 and around pulleys 46 mounted to support columns 48 in the dock building, as shown in FIG. 1. They are attached at their other ends to clew plates 50. Each clew plate 50 can accommodate up to seven or eight winch cables 34, and is attached by a winch chain 52 to a winch 54, as shown in FIG. 1. Winches 54, draw down the clew plates 50 with the winch chains 52, enabling each approximately fifty foot section of the frame 12 to be lifted at twelve or more points. Some of these points are shared with other sections along trusses 28 as required, as shown in FIG. 3.

In the operation of this prior art embodiment, the fumigation tent shown in the aforesaid Figures is raised by reeling in the clew plates 50 with the winches 54, such that the side curtains 18 are drawn upward by winch cables 34 via pulleys 44 and 46. As the winch cables 34 are drawn upward the horizontal pipes 30 on the first interval rise upward. This causes the rings 36 around the winch cables 34 between the first and second intervals of pipes to gather together, thus supporting and collecting intermediate portions of the side curtains 18, and thus preventing the side curtains 18 from "bagging out", i.e., overhanging, to half the height of the side walls of the tent. The rings 36, horizontal pipes 30, and pockets 32 distribute this bagout into several smaller bagouts located between the rings that surround the winch cables 34, so that the overhang created when the tarp 14 is completely gathered up is minimized, as shown in FIG. 5.

Once the first interval of horizontal pipes 30 is drawn up to the height of the second interval, the rings between the second and third intervals gather together supporting and collecting the intermediate portions of the side curtains 18. This process continues until all the horizontal pipes 30 and rings 36 are drawn up against the underside 12' of the frame 12. Once the side curtains 18 have been completely raised, and the tarp 14 collected, the winches 54 continue to draw up the winch cables 34, thus raising the frame 12. The winch cables 34 are drawn up until the frame 12 reaches a height which will enable forklift trucks to remove the pallets of produce without interfering with the fumigation tent. From the height where the side curtains 18 are completely gathered up to the height the frame 12 is finally raised to, the support cables 22, dead-tied to the roof of the dock building, become limp, i.e., in this interval the frame 12 is supported by the winch cables 34, as shown in FIG. 5.

This prior art fumigation tent is lowered by similar moves for raising the tent described above, except reversing the procedure by reversing the winches, etc. to have the cables, pulleys, etc. operate in the opposite paths as described.

Figure 6:
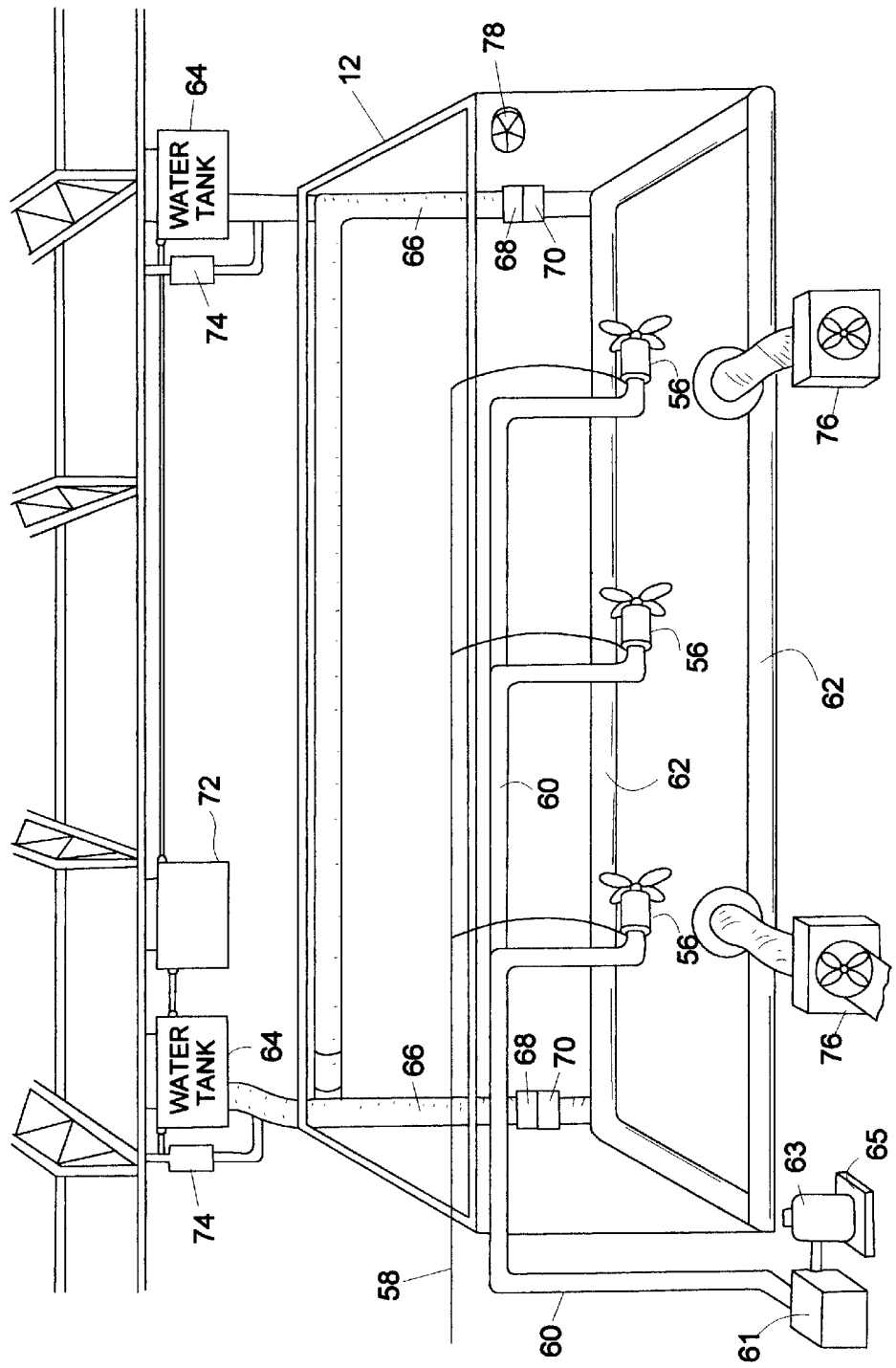
FIG. 6 shows the prior art fumigation tent described above in its lowered positioned, a water supply and removal system, circulation and exhaust fans with their associated wiring, and components of the gas supply system.

Mounting fans 56 and associated wiring 58 on frame 12 is shown in FIG. 6. Entrance hoses 60 for supplying a fumigation gas are positioned near designated fan locations to insure dispersion by mixing concentrated heated gas into the accelerated airstream provided by fans 56. A portion of these hoses rise with the tent, requiring couplings to be made with gas heaters 61 when the tent is lowered. A fumigation gas tank 63, which rests on a beam balance scale 65, supplies the fumigation gas to the heater 61. Once the tent is in place over the pallets of produce, it must be sealed to the floor of the dock building to create a substantially airtight enclosure, and thus prevent fumigation gas from escaping into the dock building during the fumigation process.

In the disclosed prior art, the method of sealing the tent to the dock floor, is to mount a flexible hose 62 along the bottom perimeter 20 of the tent and fill the hose with water, as shown in FIGS. 4 and 6. The weight of the water secures the tent to the floor of the dock building. The water can be reused by storing it in elevated tanks 64 located above the tent, preferably mounted to the roof of the dock building, as shown in FIG. 6. Collapsible flexible hoses 66 supply water from the elevated storage tanks 64 to the flexible perimeter hose 62. One-way foot valves 68 connected to the collapsible flexible hoses are employed to control columns of water to start the Venturi acceleration process for evacuation of the water from the perimeter hose 62. The foot valves 68 are by-passed by solenoid valves 70 to permit gravity filling of the hose. A compressor 72 supplies air pressure to the tops of the elevated storage tanks 64 to assist in the gravity filling of the flexible perimeter hose 62. Upon returning the water to the tanks, the compressor 72 blows the water from the hose 62 toward the foot valve location where it is carried up by the Venturi.

A water removal system is provided for evacuating the water from the flexible perimeter hose 62 comprising jet pumps 74 located above the tent, preferably mounted to the roof of the dock building, using low-mounted Venturi units which shoot the water up the collapsible flexible hoses 66 into the elevated storage tanks 64. Four distributed storage tanks limit the spilled water to one-quarter of the system'capacity. The compressor 72 can also supply air pressure through the collapsible flexible hoses 66 to assist in evacuating the water from the flexible perimeter hose 62, so that sections of the flexible perimeter hose do not collapse and trap water, thus preventing total water removal.

Once the fumigation process is complete, the fumigation gas is removed by exhaust fans 76 positioned on the floor of the dock building. These fans 76 are used to evacuate the interior of the fumigation tent before the tent is raised. Openings 78 in the tent re-introduce fresh air, as shown in FIG. 6. After approximately two hours of aeration, the tent is raised. It then takes approximately one additional hour for the fumigation gas to disperse to the level where dock personnel can enter the tent area safely.

The foregoing detailed description of the prior art preferred fumigation tent system has many advantages, and the overall concepts therein are incorporated into the present invention.

As will be recognized by those skilled in the art, the present invention is not limited to fumigating produce. It can be used to fumigate any article or object that can be placed under the tent. Furthermore, it is contemplated that the present invention can be adapted to be transportable.

Figure 7:
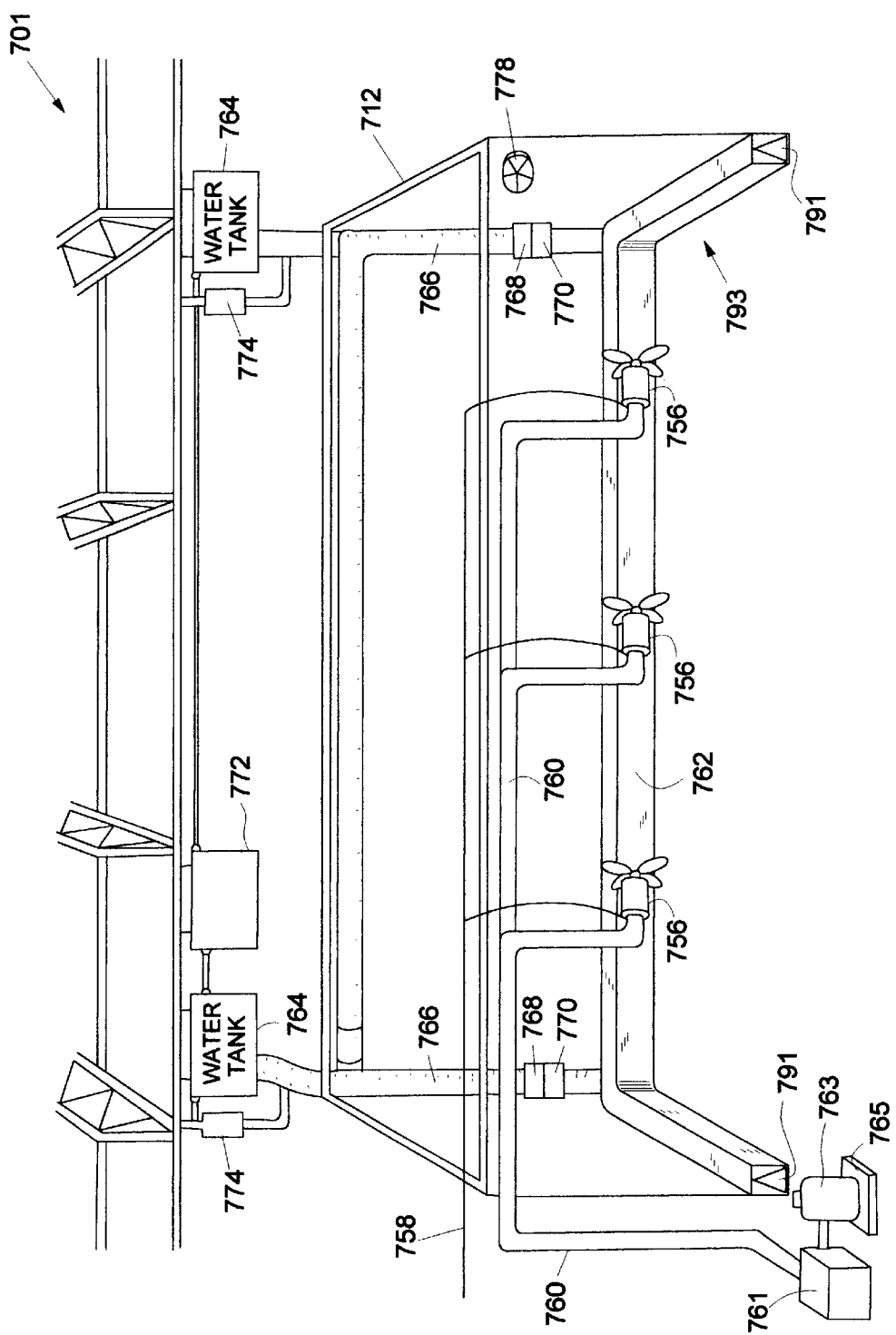
FIG. 7 shows a perspective view of a present invention fumigation tent, which includes a composite closing structure for sealing the bottom perimeter of the curtains and having a triangular structural support component.

FIG. 7 and FIG. 8 show a present invention composite closing structure 793 for sealing the bottom perimeter of side curtains and having a triangular structural support component 791. Similar parts are numbered as in FIG. 6, but beginning with "700". The function of these parts is as described by FIG. 1 through FIG. 6.

In addition, the composite closing structure 793 is connected to the bottom perimeter of the side curtains, as shown and described in FIG. 4. The composite closing structure 793 has at least a first component and second component. The first component is the structural support component 791 and has sufficient rigidity to flex no greater than 6 inches over a 10 foot length with a fulcrum weight of 100 pounds.

As shown in FIG. 7, the structural support component 791 has a triangular cross section. However, other embodiments of the structural support component are disclosed, as described hereinafter below. The structural support component 791 may be made from metal, wood, plastic and the like.

The second component is a sealing component 762 and is formed of flexible material. The sealing component 762 may be flexible hosing, flexible synthetic foam, flexible rubber, rubber foam, and the like. It may be located within the composite closing structure 791 or be part of the outer material. As shown, the sealing component 762 is a flexible base which may be mounted along the bottom perimeter of the side curtains for receiving, holding and releasing water from an external water supply. When the sealing component holds water, it will seal the tent to a floor.

In an alternative embodiment, the sealing component 762 may be lowered onto the top of the side curtains after being placed partially on the floor and fold away from the tent center. In this way, the sealing component 762 would act to physically compress the curtain bottom against the floor.

FIG. 9 and FIG. 10 show front cross sectional views of another embodiment of a present invention composite closing structure 1605 and 1705, respectively. The composite closing structure 1605 includes a sealing component 1651 and a structural support component 1653. The structural support component includes a hook 1657 and an eyelet 1655, on each end of the structural support component 1653, for removably connecting each composite closing structure 1605, 1705 to at least one other composite closing structure. The hook 1657 and the eyelet 1655 may be reversed having the hook protruding from the composite closing structure 1605 and the eyelet located within the composite closing structure 1605. component.

The composite closing structure 1705 is similar to that described in FIG. 9. Similar components are similarly numbered to those described by FIG. 9, but beginning with "1700".

FIG. 11 and FIG. 12 show front cross sectional views of another embodiment of two composite closing structures 1805, 1905, respectively, of the present invention. The composite closing structure 1805 includes a sealing component 1851 and a structural support component 1853. The structural support component 1853 has a link 1855 for removably connecting each composite closing structure 1805, 1905 to a link 1955 on at least one other composite closing structure.

The composite closing structure 1905 is similar to that described in FIG. 11. Similar components are similarly numbered to those described by FIG. 15, but beginning with "1900".

Referring now to FIG. 13, there is shown a front cross sectional view of another embodiment of a composite closing structure 2002 of the present invention. The composite closing structure has a single structural support component 2053 within a single sealing component 2051. Note that, in this embodiment, the structural support component 2053 can be located in any placement within the sealing component 2051.

Figure 14:
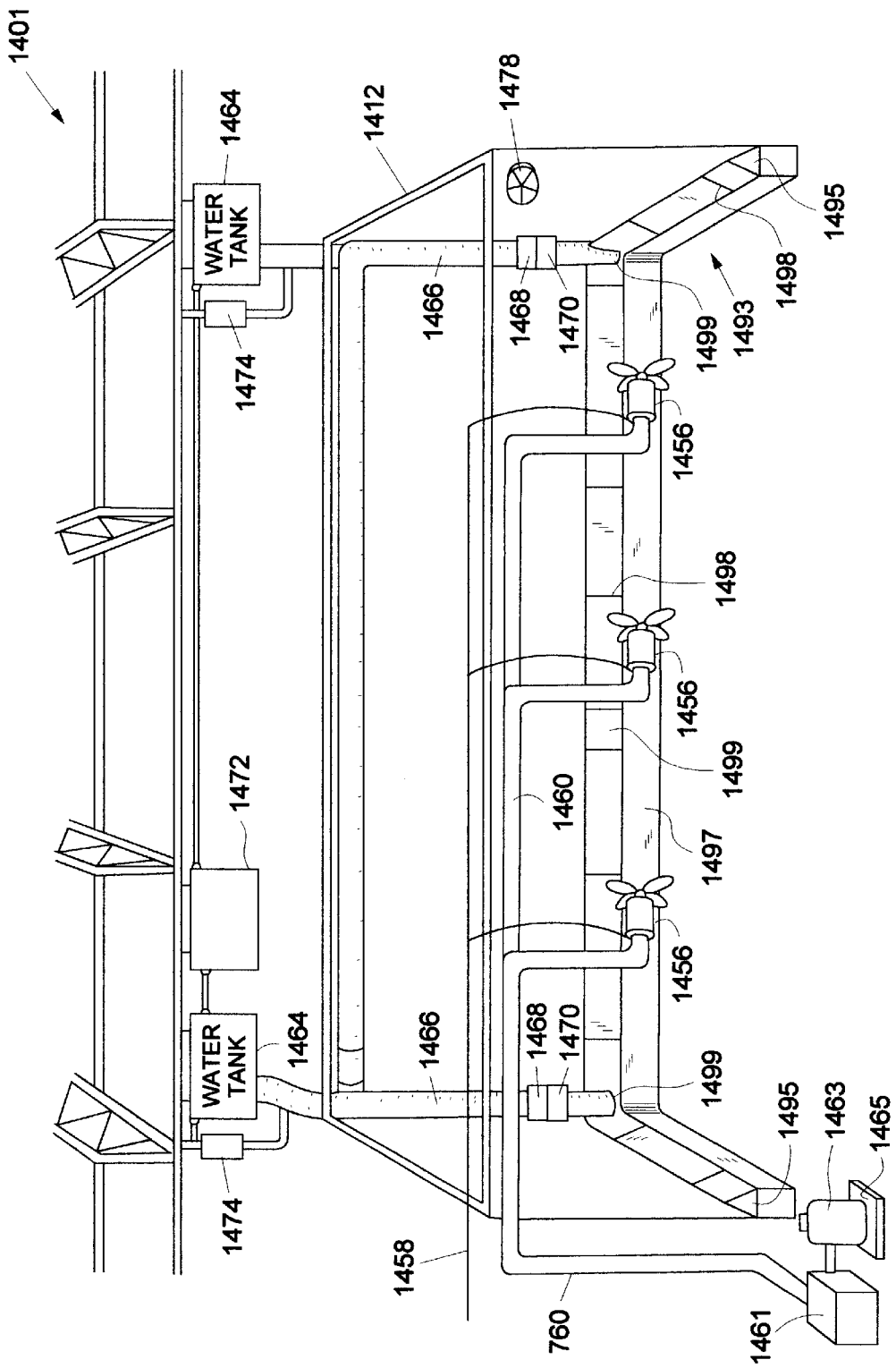
FIG. 14 shows a perspective view of an alternative embodiment present invention fumigation tent, which includes a composite closing structure having a structural support component external to a sealing component.

FIG. 14 shows a perspective view of an alternative embodiment present invention fumigation tent 1401, which includes a composite closing structure 1493 having a structural support component 1495 external to a sealing component 1497. Identical parts to those shown in FIG. 7 are numbered similarly, but beginning with "1400".

In this embodiment, the structural support component 1495 includes at least one metal rod or truss, which is connectible to the sealing component 1497 through connecting means 1498. In this case, the connecting means 1498 is a plurality of ties extending from within the sealing component 1497, which are tied around the structural support component 1495. In addition, there may be at least one flexible joint 1499 between multiple structural support components 1495.

FIG. 15 and FIG. 16 show side views of a present invention composite closing structure 1496 and 1593, respectively, which may be used in combination with the fumigation tent shown in FIG. 14. In FIG. 15, the structural support component 1495 has a triangular cross-section while in FIG. 16, the structural support component 1596 has a circular cross-section. In FIG. 16, identical parts to those shown in FIG. 14 are similarly numbered, but beginning with "1500".

FIG. 17 shows sample external water supply mechanism. Here, it is a portable, mobile system which includes a water tank and a pump tank. Often multiple tents are not used simultaneously and the previous system of having tanks and pumping equipment dedicated to each of them has been improved by providing a portable pumping and water supply system usable at various tent locations. This saves costs and installation and maintenance manpower.

This portable apparatus functions substantially as the previous system described in prior art except that the water is delivered from a separate external source and the pump pressures may be reduced as the lift head is less and the foot valves and venture nozzles would not be required. Initial investment is reduced for each tent as the result of shared facilities. Composite closing structure 793 of FIG. 7, when the tents sides are fully extended, rests on the dock building floor. To prevent water ponding, and in the winter icing, the floor of the dock is typically sloped downward toward the sea, e.g., approximately 18 inches downward for every 100 foot measure perpendicular to the sea-wall. This floor condition requires the water truck connection to be located at the lower point on the perimeter of the composite closing structure 793. Complete drainage pumping and filling are facilitated by working with gravity. Tank 1700 has an excess if capacity of the largest perimeter composite closing structure volume. A pump 1702 with valving for pressure and suction device connects to service hose 1703. Air pump 1701 hastens water delivery.

Obviously, numerous modifications and variations of the present invention are possible in light of the above teachings. For example, any type of connecting means may be used for connecting the structural component to the sealing component, or vice versa. Moreover, the structural support component may be connected in any position relative to the sealing component, i.e., above, within, adjacent or below. It is therefore understood that within the scope of the appended claims, the invention may be practiced otherwise than as specifically described herein.

What is claimed is:

1. A mechanized fumigation tent, which comprises:
   (a) a structure;
   (b) support cables communicating with said structure;
   (c) a frame suspended from said structure by said support cables, said frame having an underside;
   (d) a tarp adapted to be mounted to the underside of the frame, said tarp hanging from said frame defining a tent having a top and side curtains having a lower periphery that defines a bottom perimeter;
   (e) a plurality of horizontal pipes attached to, and arranged along, said side curtains of said tent at spaced intervals between said bottom perimeter and said top of the said tent;
   (f) a plurality of winch cables for raising said horizontal pipes;
   (g) rings, disposed around said winch cables and attached to said horizontal pipes, for gathering up and supporting the tarp as the horizontal pipes are raised, said rings and horizontal pipes cooperating with each other to collect the tarp into a plurality of small overhanging portions;
   (h) a composite closing structure being one of connected to said bottom perimeter of said side curtains and physically compressing against the floor, wherein said composite closing structure seals said bottom perimeter of said side curtains, said composite closing structure having at least a first component and second component, said first component being a structural support component and having sufficient rigidity to flex no greater than 6 inches over a 10 foot length with a fulcrum weight of 100 pounds, and said second component being a sealing component and being formed of flexible material; and 2. The mechanized fumigation tent of claim 1 wherein said sealing component is selected from the group consisting of flexible hosing, flexible synthetic foam, flexible rubber and rubber foam.

3. The mechanized fumigation tent of claim 2 wherein said sealing component is a flexible base mounted along said bottom perimeter for receiving, holding and releasing water from an external water supply, whereby when holding water, will seal said tent to a floor.

4. The mechanized fumigation tent of claim 1 wherein said structural support component is formed of a triangular cross-sectional shape.

5. The mechanized fumigation tent of claim 2 wherein said structural support component is formed of a triangular cross-sectional shape.

6. The mechanized fumigation tent of claim 1 wherein said structural support component is selected from elongated metal sections, elongated wood sections and elongated plastic sections.

7. The mechanized fumigation tent of claim 4 wherein said structural support component is an integral metal rod.

8. The mechanized fumigation tent of claim 6 wherein said structural support component is selected from the group consisting of a plurality of metal rods and a plurality of trusses wherein each one of said metal rods and said trusses have connecting means for connecting one said structural support component to another said structural support component.

9. The mechanized fumigation tent of claim 8 wherein said connecting means includes one of eyelets and hooks, and interlocking links.

10. The mechanized fumigation tent of claim 2 wherein said structural support component is selected from the group consisting of a plurality of metal rods and a plurality of trusses wherein each one of said metal rods and said trusses have connecting means for connecting one said structural support component to another said structural support component.

11. The mechanized fumigation tent of claim 10 wherein said connecting means includes one of eyelets and hooks, and interlocking links.

12. The mechanized fumigation tent of claim 11 wherein each of said winch cables passes through a pair of guide tubes and is fixed to a plate mounted on said frame.

13. The mechanized fumigation tent of claim 1 wherein a cross-sectional shape of said structural support component is selected from the group consisting of circular, triangular, rectangular, hexagonal and rectangular.

14. The mechanized fumigation tent of claim 2 wherein a cross-sectional shape of said structural support component is selected from the group consisting of circular, triangular, rectangular, hexagonal and rectangular.

15. The mechanized fumigation tent of claim 1 wherein said structural support component is embedded within said sealing component.

16. The mechanized fumigation tent of claim 2 wherein said structural support component is embedded within said sealing component.

17. The mechanized fumigation tent of claim 1 wherein said structural support component is removably connected to said sealing component.

18. The mechanized fumigation tent of claim 2 wherein said structural support component is removably connected to said sealing component.

19. The mechanized fumigation tent of claim 1 wherein a flexible joint is located between said structural support components.

20. The mechanized fumigation tent of claim 2 wherein a flexible joint is located between said structural support components.

* * * * *